US00PP26210P3

(12) United States Plant Patent
Pierron-Darbonne

(10) Patent No.: US PP26,210 P3
(45) Date of Patent: Dec. 15, 2015

(54) STRAWBERRY PLANT NAMED 'DREAM'

(50) Latin Name: *Fragaria×ananassa*
Varietal Denomination: Dream

(71) Applicant: Darbonne Pepiniere, SAS, Le Barp (FR)

(72) Inventor: Alexandre Pierron-Darbonne, Navarra (ES)

(73) Assignee: Darbonne Pepiniere, SAS (FR)

( * ) Notice: Subject to any disclaimer, the term of this patent is extended or adjusted under 35 U.S.C. 154(b) by 3 days.

(21) Appl. No.: 13/987,148

(22) Filed: Jul. 3, 2013

(65) Prior Publication Data

US 2015/0020249 P1 Jan. 15, 2015

(30) Foreign Application Priority Data

Jul. 5, 2012 (QZ) ..... PBR 2012/1503

(51) Int. Cl.
*A01H 5/08* (2006.01)

(52) U.S. Cl.
USPC ..... Plt./209
CPC ..... *A01H 5/0893* (2013.01)

(58) Field of Classification Search
USPC ..... Plt./208, 209
CPC ..... A01H 5/0893
See application file for complete search history.

(56) References Cited

FOREIGN PATENT DOCUMENTS

| | | |
|---|---|---|
| CH | 13-2901 | 9/2013 |
| ES | 20120165 | 6/2012 |
| QZ | 2012/1503 | 7/2012 |

OTHER PUBLICATIONS

UPOV Record Detail, 'Dream', retrieved Oct. 23, 2014.*
"PLANASA presenta dos nuevas variedades de fresa" dated Aug. 30, 2013, downloaded from Fresh Plaza on the world wide web at www.freshplaza.es/article/75890/Espa%C3%B1a-PLANASA-presenta-dos-nuevas-variedades-de-fresa (with English translation).
"La variedad de Planasa, Dream, triunfa en SIVAL 2013 Jan. 21, 2013" dated Jan. 21, 2013, downloaded from Planasa on the world wide web at www.planasa.com/index.php?m=48&subm=58&id=85&pagina=7 (with English translation).

* cited by examiner

*Primary Examiner* — Keith Robinson
(74) *Attorney, Agent, or Firm* — Knobbe, Martens, Olson & Bear, LLP

(57) ABSTRACT

A new and distinct strawberry variety, *Fragaria×ananassa*, cv. 'Dream' is characterized by a red to dark red fruit color (RHS red group (near 43 B to 44 A)), a large fruit size, an open density, and a medium vigor.

12 Drawing Sheets

Latin name of the genus and species claimed: *FRAGARIA× ANANASSA*.

Variety denomination: 'DREAM'.

BACKGROUND AND SUMMARY OF THE INVENTION

The present invention relates to a new and distinct strawberry variety. The varietal denomination of the new variety is 'Dream'. The new variety was designated by the breeder as 'Dream (DA50)'. The new variety of strawberry was created in a breeding program by crossing two parents in 2007 in Le Barp, France; in particular, by crossing as seed parent an undistributed strawberry parent designated "31.14.04" (unpatented) and as pollen parent an strawberry parent designated "01.12.52" (unpatented). Seed parent and pollen parent are selections from the breeder's program and have not been commercialized.

The resulting seedling of the new variety was grown and asexually propagated by runners in Le Barp, France 0.7° W., 44°, 50 meters elevation. Propagation by runners included propagation by runners, separately for each varieties, first into a Screen-House, and after in the fields. Clones of the new variety were further asexually propagated and extensively tested. Each variety was reproduced by stolons in the nurseries. In order to establish and bring to health the initial head clones, mother plants that had developed several stolons were subjected to a heat treatment, or thermoterapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing has demonstrated that the combination of traits disclosed herein which characterize the new variety are fixed and retained true to type through successive generations of asexual reproduction.

Among the characteristics which appear to distinguish the new variety from its closest variety of which I am aware, 'Clery' (unpatented in the US), is a combination of traits which include: serrate terminal leaflet incisions in the new variety as compared to crenate for 'Clery' (unpatented in the US). The new variety also has a darker red to dark red fruit color (RHS red group (near 43 B to 44 A)), as compared to red (RHS red group near 40 B to 41 A) for 'Clery' (unpatented in the US). The luminosity for the fruit of the new variety at 460 nm observed on May 7 was 56.7, as compared to 43.5 for 'Clery' (unpatented in the US). The new variety also has a large fruit size as compared to medium for 'Clery'(unpatented in the US). The average fruit mass (g/fruit) observed for 'Dream' on May 7 was 23.5 g, compared to 18.9 g for 'Clery'. It is noted that 'Clery' is an unpatented variety in the US. In The European Union, 'Clery' is patented as: EU 16743.

Characteristics which appear to distinguish the new variety from the variety 'Darselect' as characterized in U.S. Plant Pat. No. 10,402, at least include that the new variety has an open density and a medium vigor.

The new variety is distinguished from its parents by the following characteristics possessed by 'Dream' which are different than, or not possessed, by the seed parent designated "31.14.04" (unpatented) and pollen parent strawberry designated "01.12.52" (unpatented): (1) Seed parent "31.14.04" (unpatented) is more vigorous than the plant of the new variety "Dream"; (2) In seed parent "31.14.04" (unpatented) the production of commercial quality fruit is smaller than in the new variety "Dream"; (3) In the seed parent "31.14.04" (unpatented) the fruit size is bigger than in the new variety "Dream"; (4) In the pollen parent "01-12-52" (unpatented) the fruit size is smaller than in the new variety "Dream"; (5) Pollen parent "01-12-52" (unpatented) shows a fruit glossiness less intense than in the new variety "Dream".

BRIEF DESCRIPTION OF PHOTOGRAPHS

The accompanying photographs show typical specimens of the new variety, designated 'Dream' or 'DA 50' in the illustrations, including fruit, foliage and flower, in color as nearly true as it is reasonably possible to make in color illustrations of this character.

DESCRIPTION OF THE NEW VARIETY

Figure 1:
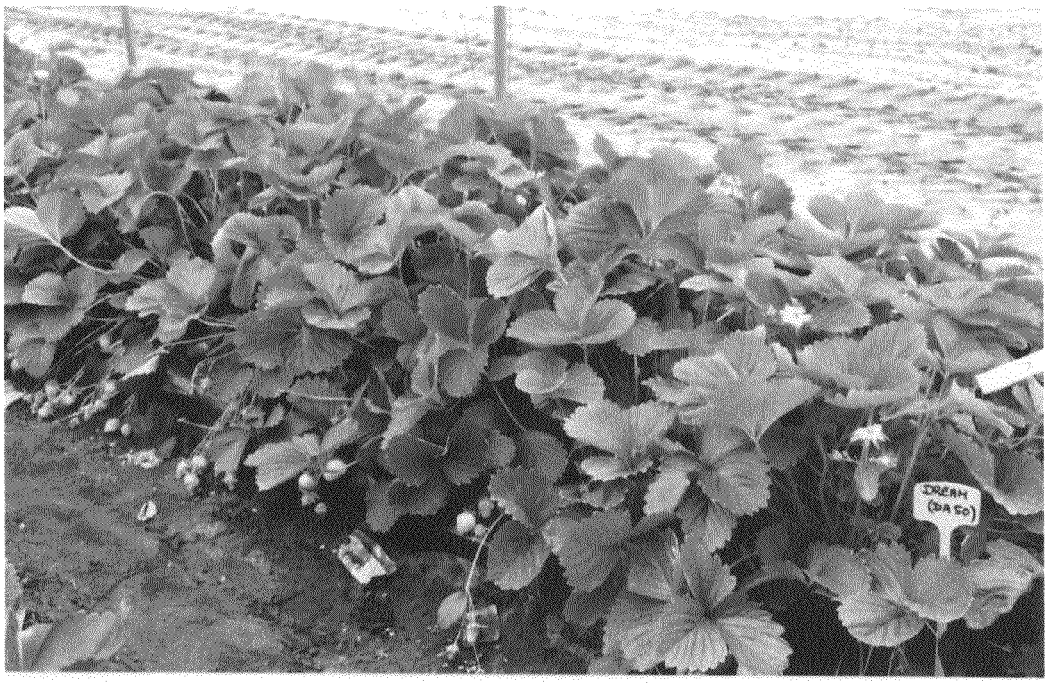
FIG. 1 shows several plants of the new variety 'Dream.'
Figure 2:
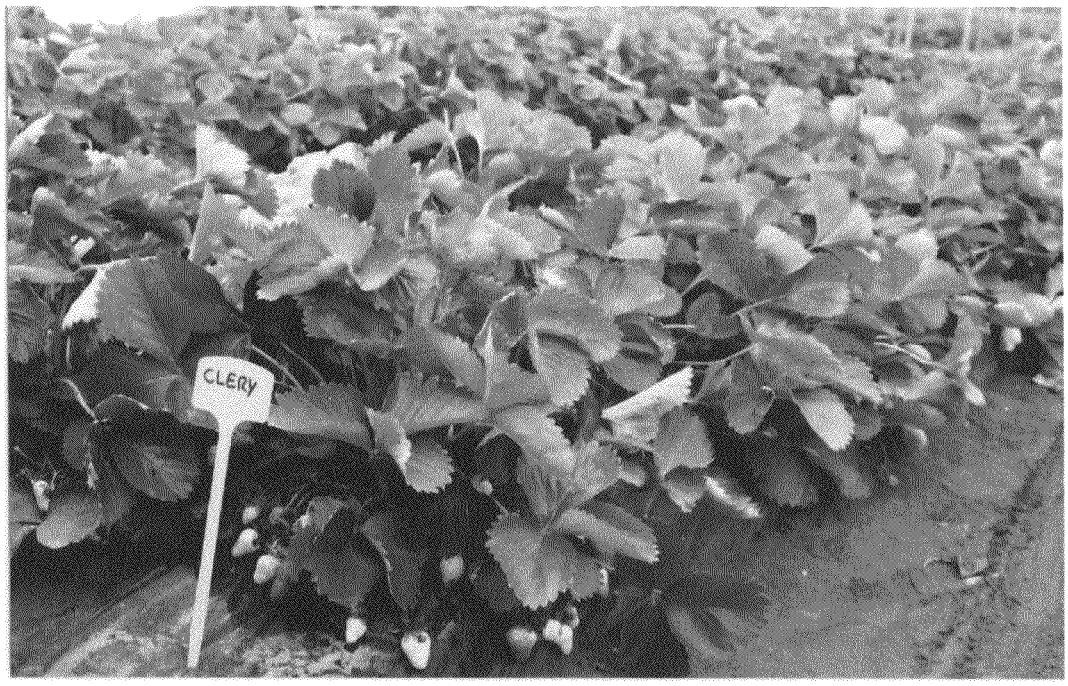
FIG. 2 shows several plants of the closest variety, 'Clery.'
Figure 3:
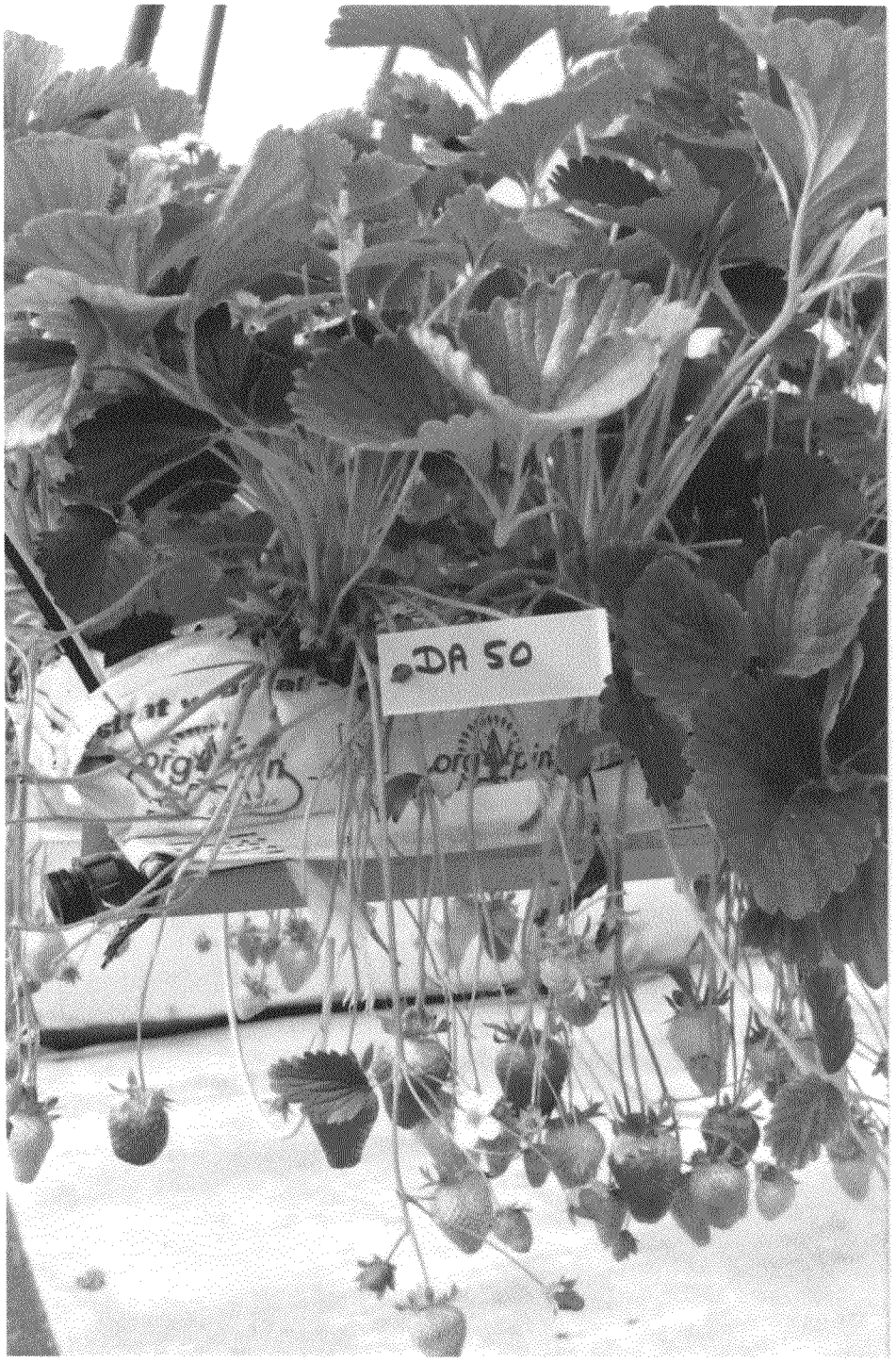
FIG. 3 shows several plants of the new variety of 'Dream' with several red (RHS red group (near 43 B to 44 A)) colored and conical shaped fruits.
Figure 4:
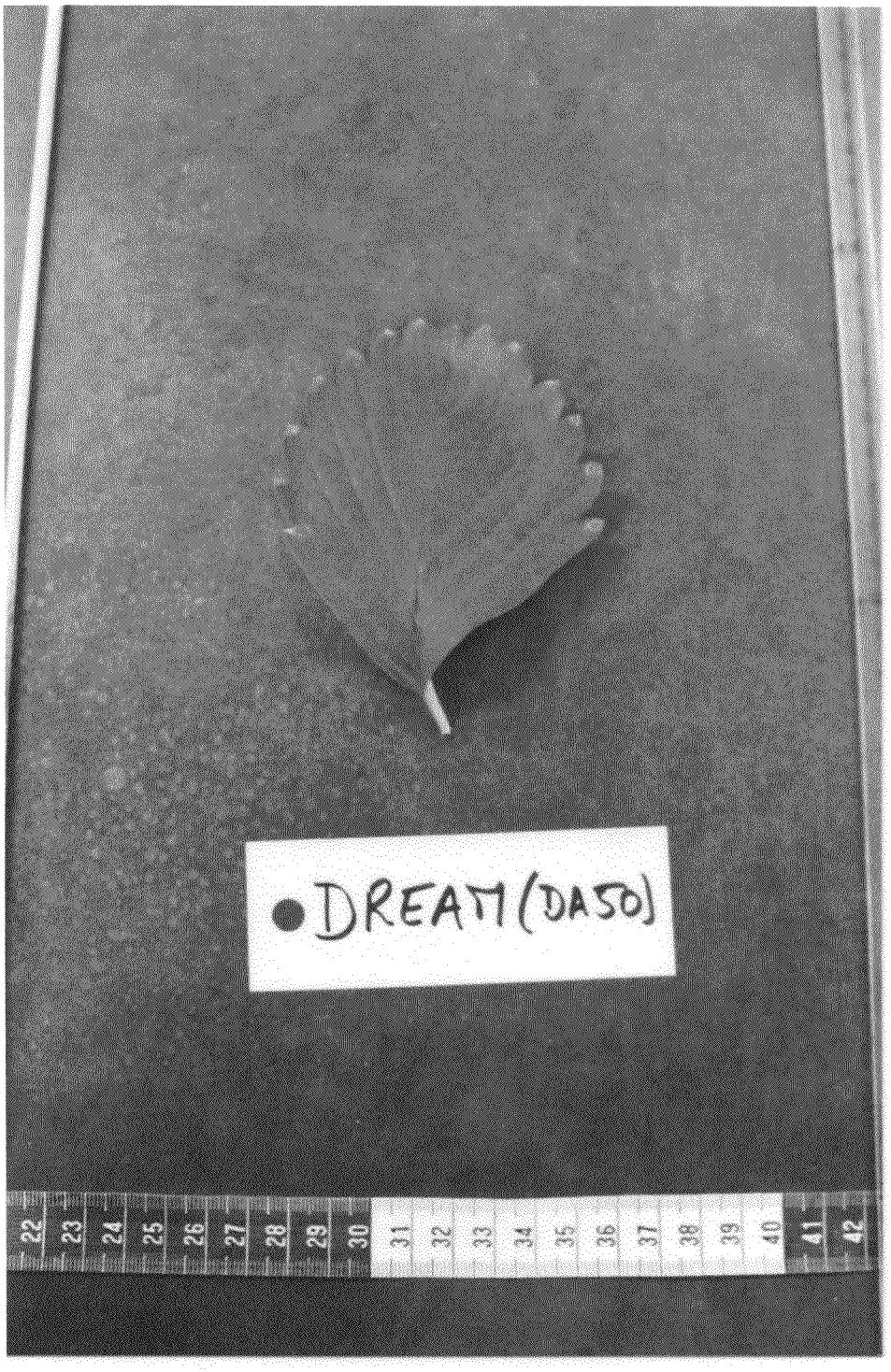
FIG. 4 shows the upper side of a terminal leaflet of the new variety 'Dream.' A medium green color (RHS yellow-green group color (near 144 A to 146 B)), and serrate shapes of incisions at the margins of the terminal leaflets can be seen.
Figure 5:
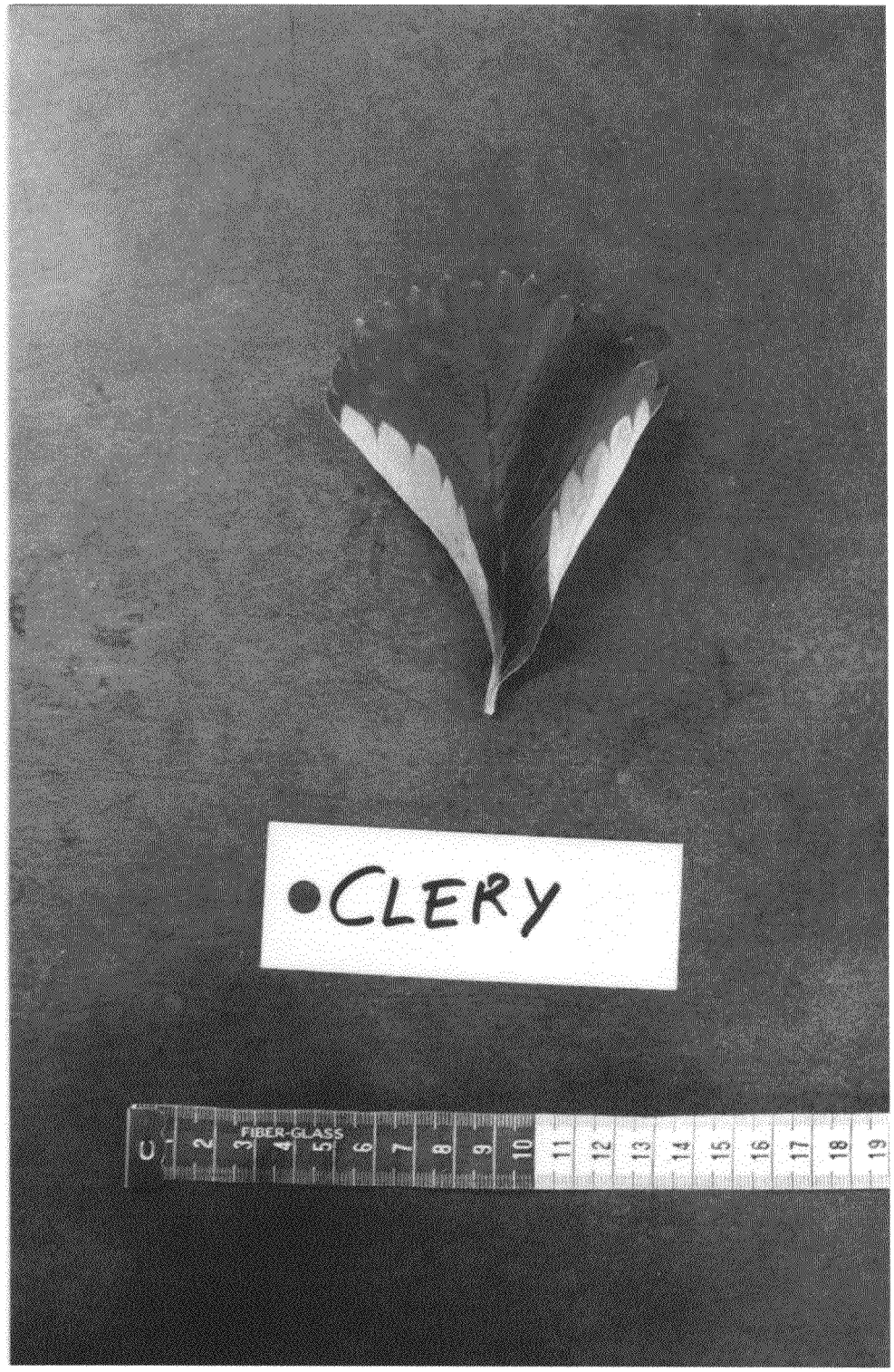
FIG. 5 shows the upper side of a terminal leaflet of the variety 'Cleary.' Crenate shapes of incisions at the margins of the terminal leaflets can be seen.
Figure 6:
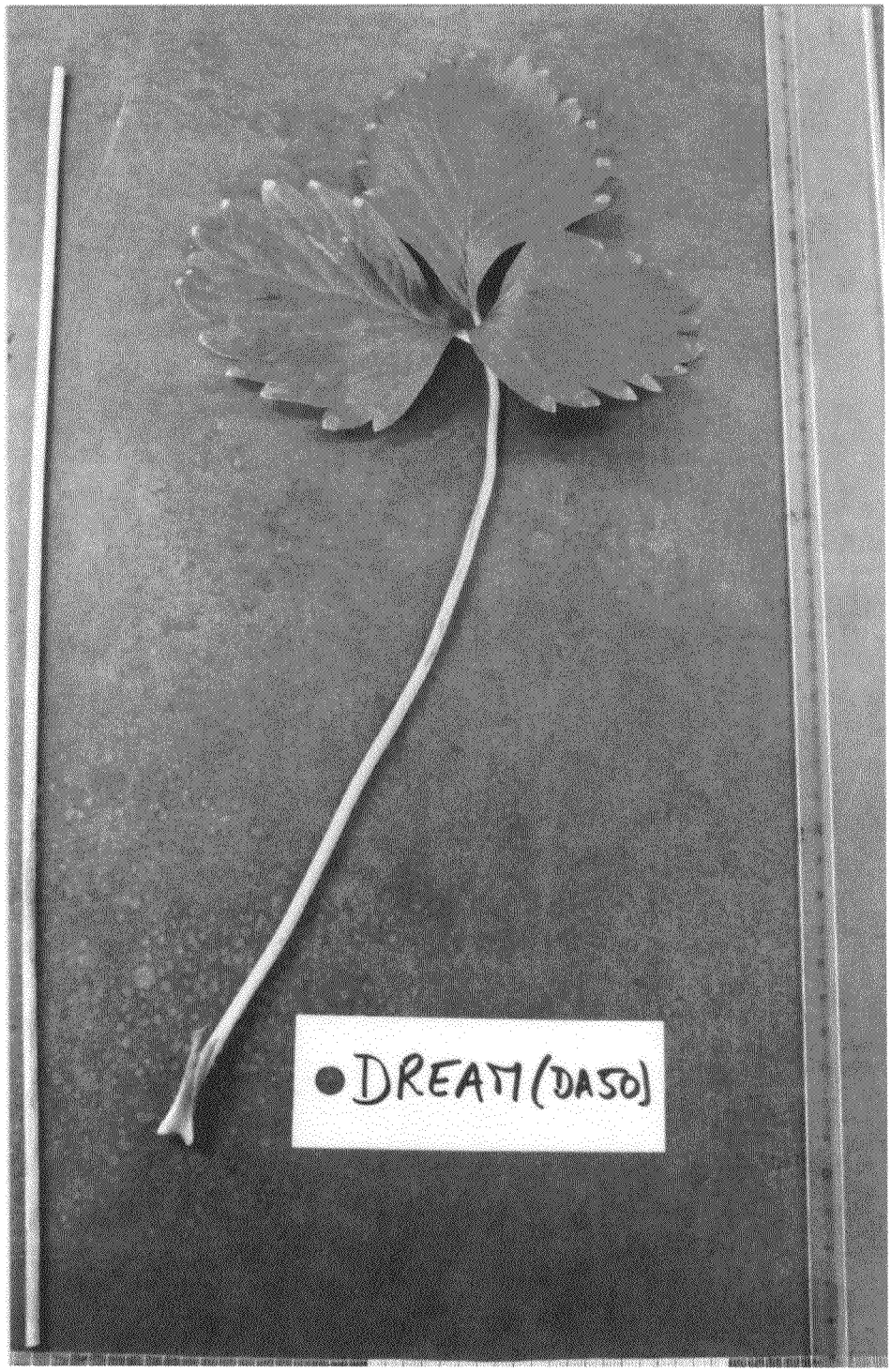
FIG. 6 shows the upper side of a complete leaf of the new variety 'Dream.' A slightly concave cross-section can be seen.
Figure 7:
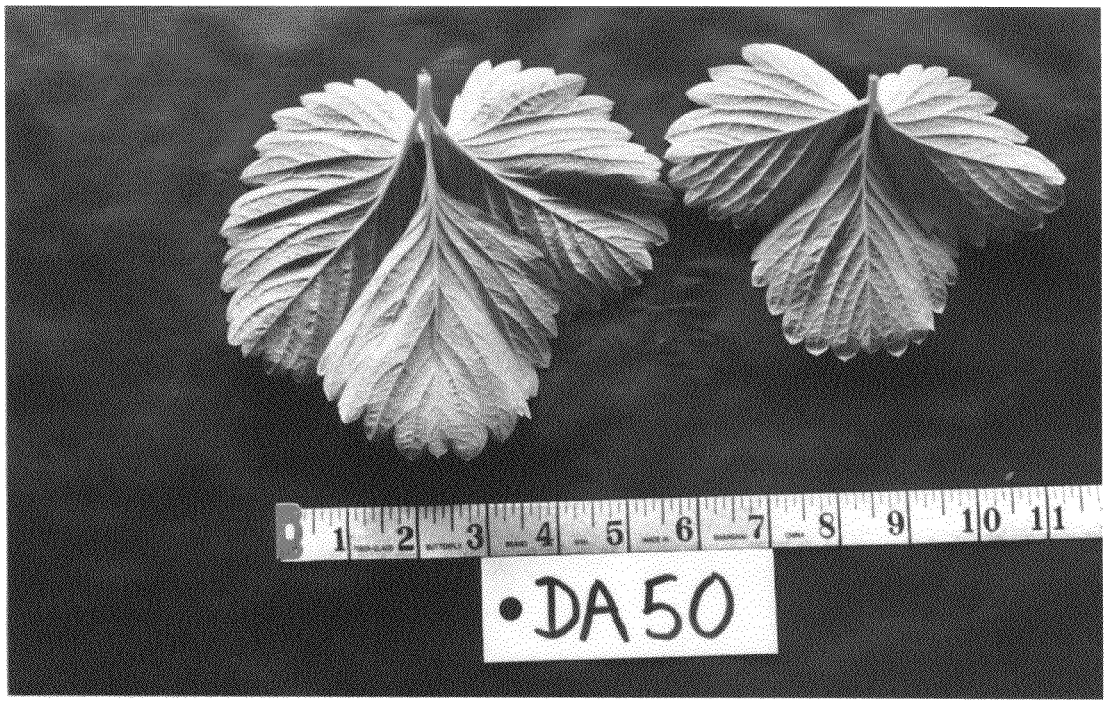
FIG. 7 shows the lower side of a complete leaf of the new variety, 'Dream.'
Figure 8:
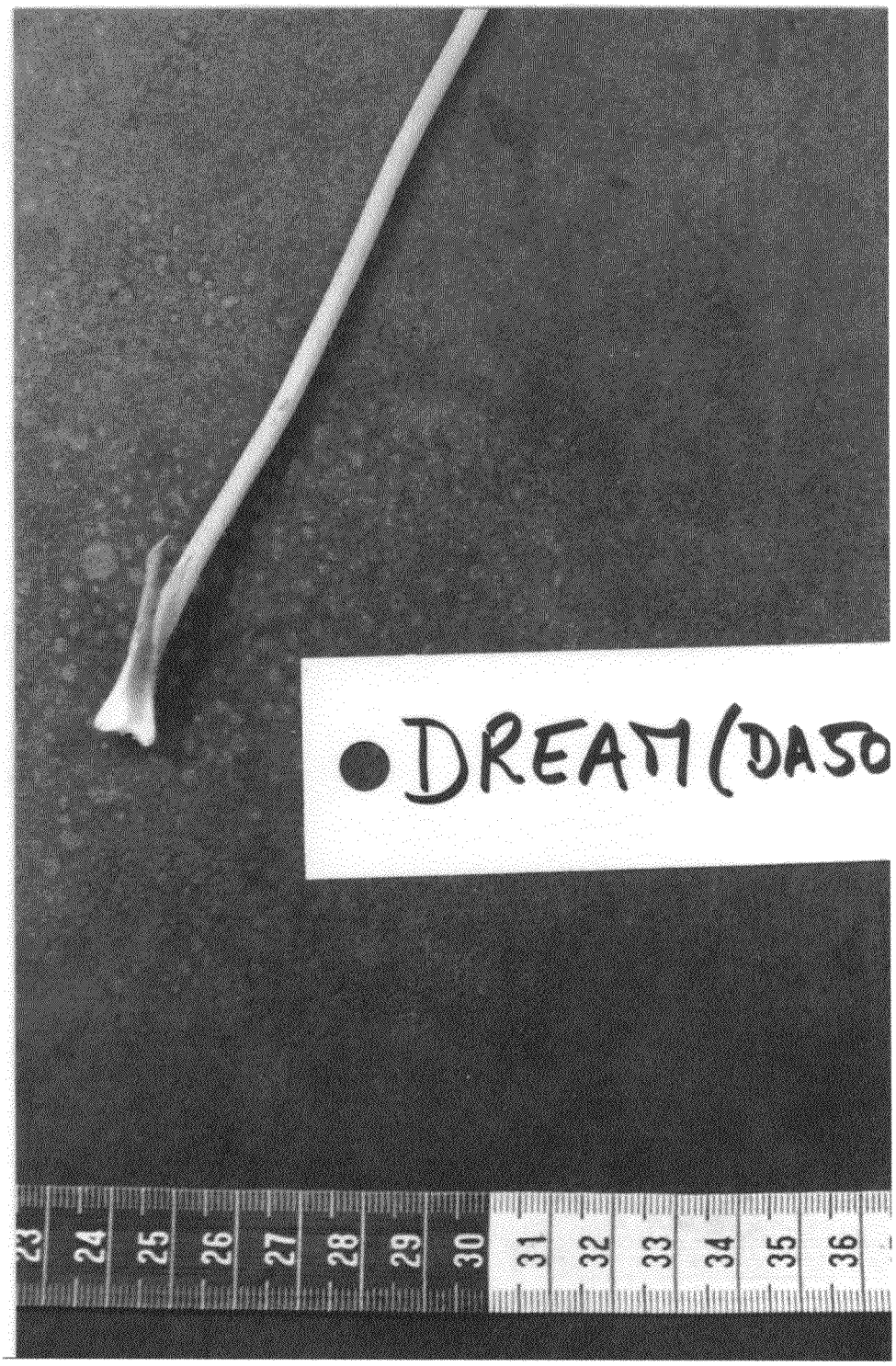
FIG. 8 shows the stipule and petiole of the new variety, 'Dream.'
Figure 9:
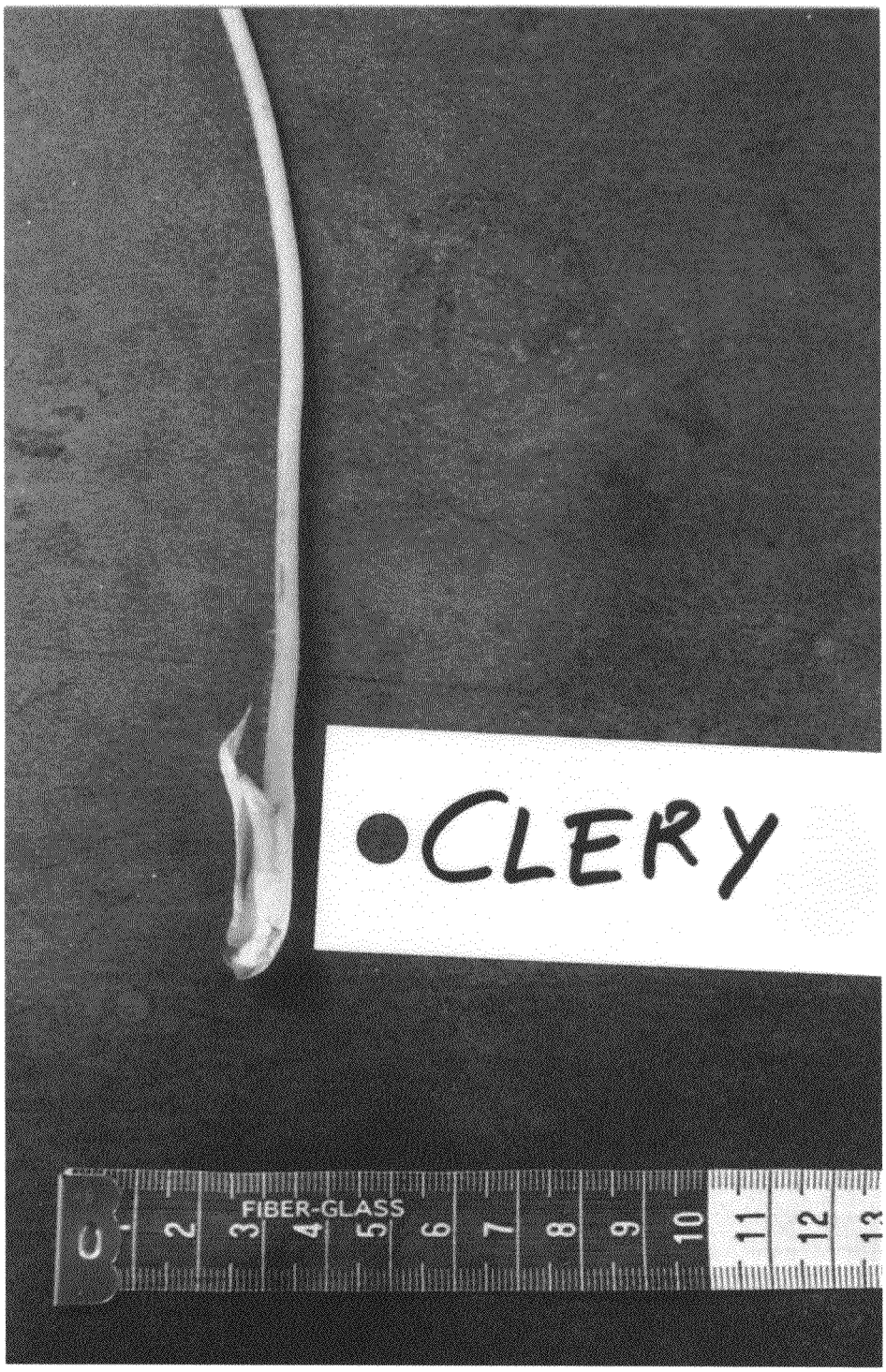
FIG. 9 shows the stipule and petiole of the variety 'Clery.'
Figure 10:
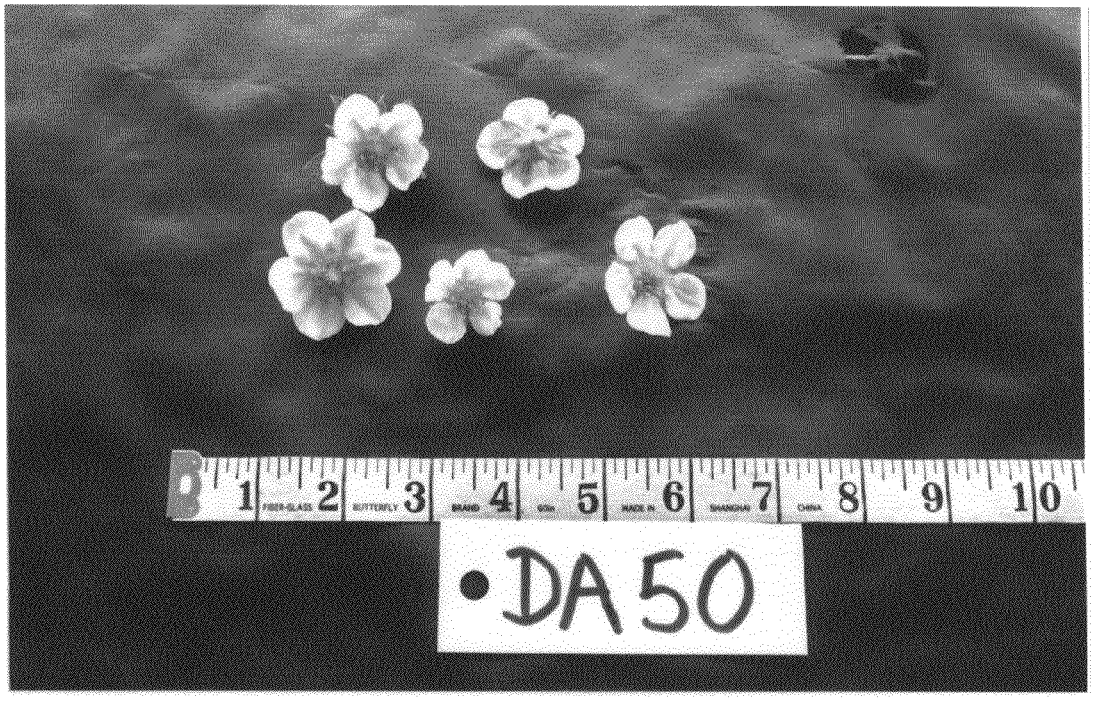
FIG. 10 shows the flowers of the new variety, 'Dream.'
Figure 11:
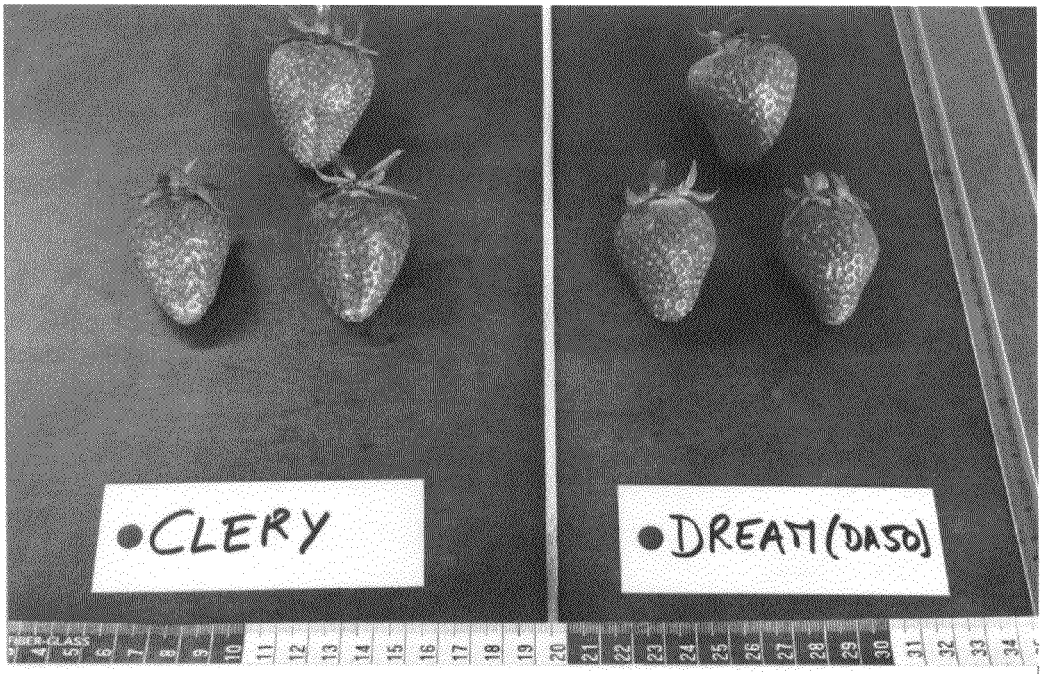
FIG. 11 shows a comparison between the varieties 'Dream' and 'Clery' that shows a typical whole fruit of both varieties, illustrating the typical conical shape, red color (RHS red group near 43 B to 44 A), and strong glossiness of 'Dream'.
Figure 12:
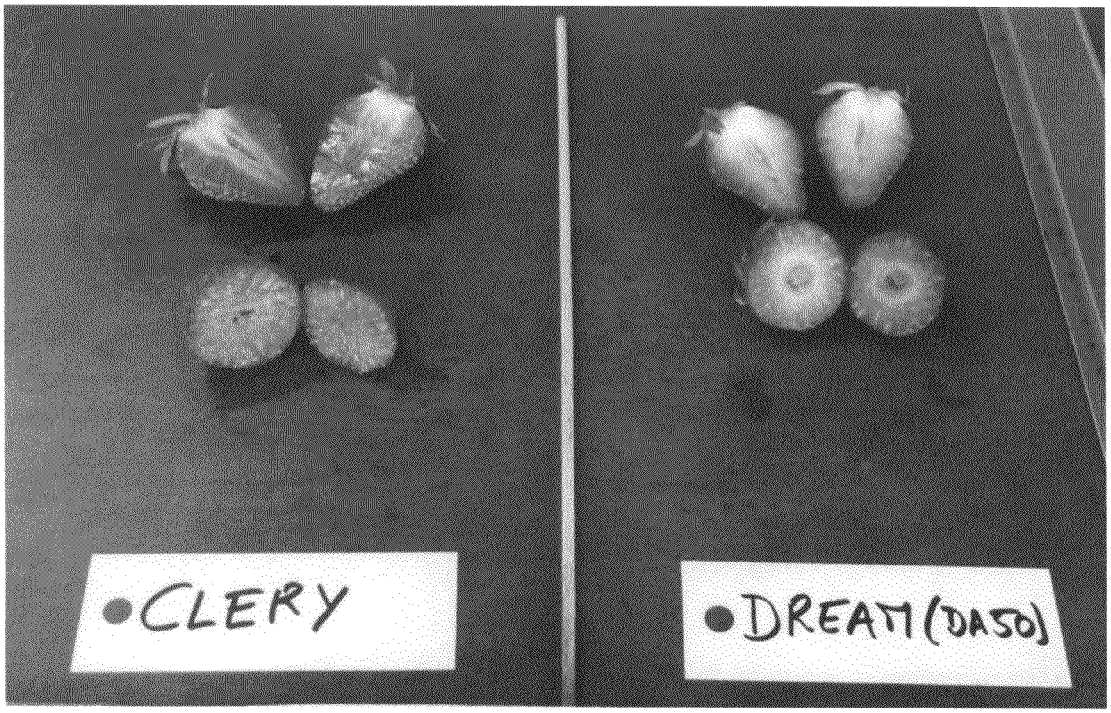
FIG. 12 shows a comparison between the varieties 'Dream' and 'Clery' that shows a typical sliced section of the fruit of both varieties illustrating the typical flesh coloration of about RHS orange-red group near 33 C to 33 A and a very weakly expressed hollow center of 'Dream'.

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown in Le Barp, France 0.7° W., 44°, 50 meters elevation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface ondulation inherent to leaves and is generally a constant characteristic.

Table 1 shows the Weight (g/Fruit) on May 7 for the new variety 'Dream,' and two varieties, 'Clery' and 'Darselect'.

TABLE 1

| WEIGHT (g/fruit)[1] | May 7 |
|---|---|
| Dream | 23.5 |
| Clery | 18.9 |
| Darselect | 24.5 |

WEIGHT is shown as the average weight per fruit in First Quality Fruits.

Table 2 shows a comparison of the fruit analysis on May 7 between the new variety 'Dream,' and two varieties, 'Clery' and 'Darselect.'

TABLE 2

| | DREAM | CLERY | DARSELECT |
|---|---|---|---|
| Humidity & Volatile Matter (%) | 92.6 | 91.5 | 91.5 |
| Dry Matter (%) | 7.4 | 8.5 | 8.5 |
| pH (to 20°) | 3.9 | 3.8 | 3.8 |
| Acidity as Anhydride Citric (%) | 0.5 | 0.6 | 0.6 |
| Soluble solids (° Brix) | 7.4 | 7.9 | 7.8 |
| Maturity Index | 14.8 | 13.2 | 13.0 |
| Dominant Tonality (nm) | 490 | 495 | 490 |
| Luminosity: Transmittance to 460 nm | 56.7 | 43.5 | 51.2 |

A. Dry Matter: It is the weight of the residual left from the trituration of the fruit after the drying process at a temperature of 103° C.$^{+}$2° C. until reaching constant weight.

$$\% \text{ Dry Matter} = \frac{\text{Weight Dry Matter}}{\text{Weight Fresh Matter}} \times 100$$

B. Humidity & Volatile Matter: Represents the content in volatile matters and water of the fruits.

$$(\%) \text{ Humidity \& Volatile Matter} = 100 - \% \text{ Dry Matter}$$

C. Maturity Index: Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

Plant:

*Growth habit*.—Semi upright.

*Habit*.—Flat globose.

*Density*.—Open.
*Vigor*.—Medium.
*Height*.—Long, about 32 cm.
*Width*.—Long, about 32 cm.

Leaf:
*Size*.—Medium.
*Length*.—About 10 to 14 cm.
*Width*.—About 12 to 15 cm.
*Color of upperside*.—RHS yellow-green group color (near 144 A to 146 B).
*Color of underside*.—RHS green group color (near 138 D to 138 C).
*Cross section*.—Slightly concave.
*Blistering*.—Weak.
*Glossiness*.—Medium.
*Variegation*.—Absent.

Terminal leaflet:
*Length/width ratio*.—As long as broad.
*Length*.—Small, about 3.8 to 4.2 cm.
*Width*.—Small, about 3.8 to 4.2 cm.
*Terminal leaflet shape of base*.—Obtuse.
*Shape of incisions at margin*.—Serrate.
*Shape in cross section*.—Slightly concave.

Petiole:
*Attitude of hairs*.—Slightly outwards.
*Length*.—Medium, about 10 to 13 cm.
*Diameter*.—About 1.5 to 2.0 mm.
*Texture*.—Slightly down and rigid.
*Color*.—RHS yellow-green group (near 145 B to 147 D).
*Pubescence*.—Slightly outwards.

Stipule:
*Size*.—Medium.
*Length*.—About 9.5 to 10.5 mm.
*Width*.—About 2.5 to 3.0 mm.
*Anthocyanin coloration*.—Weak to medium.
*Color*.—Greyed red stipule color (RHS gryed-red group near 179 B to 180 C).

Stolons:
*Number*.—Medium, about 8 to 10.
*Color*.—RHS yellow-green group (near 145 B to 147 D).
*Average diameter of stolon at bract*.—Thin, about 2 to 3 mm.
*Antocyanin coloration*.—Weak.
*Pubescence*.—Weak.

Inflorescence:
*Position relative to foliage*.—Above.

Flower:
*Size*.—Medium.
*Size of calyx relative to corolla*.—Smaller.
*Primary flower relative position of petals*.—Touching.
*Diameter primary flowers*.—Medium, about 2.2-2.6 cm.
*Diameter secondary flowers*.—Short, about 1.5-2.0 cm.
*Time from bloom to mature fruit* (*in Le Barp, France*).—About 35 to 40 days.
*Stamens*.—Present, numerous with pollen present, fertile and abundant.
*Stamen length*.—Approximately 2.5-3.0 mm.
*Color*.—RHS white group (near 155 D to 155 C).
*Color of receptacle*.—RHS red group (near 43 B to 44 A).
*Pollen*.—Fertile and abundant.
*Pollen color*.—RHS yellow orange group (near 14 B to 15 A).
*Pistils*.—Numerous, generally average in size.
*Pistil color*.—RHS yellow group (near 13 C to 13 B).
*Number of flowers per plant*.—About 50 to 55 flowers per plant.
*Anthers*.—Generally average in size.
*Anther color*.—RHS yellow group (near 13 C to 13 B) and darkening with advanced maturity.

Petal:
*Length/width ratio*.—Much broader than long.
*Length*.—Small, approximately 5 to 6 mm.
*Width*.—Medium, approximately 7 to 8 mm.
*Number of petals per flower*.—Normally about 5. No significant fragrance.
*Shape*.—Slightly ovate.
*Color*.—RHS white group (near 155 B to 155 A).
*Arrangement of petals*.—Touching.
*Texture of petals* (*both sides*).—Smooth, soft and waved.

Fruit:
*Ratio of length/maximum width*.—Slightly longer than broad.
*Peduncle length of inflorescence stem* (*primary fruit*).—About 28 to 32 cm.
*Peduncle length of inflorescence stem* (*secondary fruit*).—About 24 to 27 cm.
*Peduncle color*.—RHS yellow-green group (near 145 C to 145 B).
*Size*.—Large.
*Primary fruit length*.—Long, about 4.0 to 4.5 cm.
*Primary fruit width*.—Long, about 3.5 to 4.0 cm.
*Secondary fruit length*.—Long, about 3.5 to 4.0 cm.
*Secondary fruit width*.—Medium, about 3.0 to 3.5 cm.
*Fruit shape*.—Conical.
*Difference in shapes between primary and secondary fruits*.—Slight.
*Band without achenes*.—Absent or very narrow.
*Color of achenes*.—RHS orange red group (near 30 C to 31 A).
*Unevenness of surface*.—Weak.
*Color*.—RHS red group (near 43 B to 44 A).
*Evenness of color*.—Slightly uneven.
*Glossiness*.—Strong.
*Insertion of achenes*.—Below surface.
*Insertion of calyx*.—Level with fruit.
*Attitude of the calyx segments*.—Reflexed.
*Size of the calyx in relation to fruit diameter*.—Same size.
*Adherence of calyx*.—Strong.
*Firmness*.—Firm.
*Color of flesh*.—RHS orange-red group near 33 C to 33 A.
*Color of core*.—RHS orange-red group near 33 D to 33 C.
*Hollow center*.—Absent or very weakly expressed.
*Distribution of red colour of flesh*.—Only marginal.
*Sweetness*.—Medium. 7.4°Brix.
*Acidity*.—Medium. 0,50% (Acidity as Anhydride Citric).
*Time of flowering*.—Very early.
*Time of ripening*.—Very early.
*Type of bearing*.—Partially remontant.
*Chilling*.—About 800 hours.
*Diameter corolla primary flowers*.—About 2.2 to 2.6 cm.

*Diameter corolla secondary flowers*.—About 1.5 to 2.0 cm.

*Diameter calyx primary flowers*.—About 0.7 to 0.9 cm.

*Diameter calyx secondary flowers*.—About 0.6 to 0.8 cm.

*Insertion of calyx*.—With fruit level.

*Pose of the calyx segments*.—Reflexed.

*Adherence of calyx*.—Strong.

*Size of calyx in relation to fruit diameter*.—Same size.

*Length of sepals*.—Medium, about 3.0 to 5.0 mm.

*Width of sepals*.—Short, about 1.0 to 1.8 mm.

*Color upperside of sepals*.—RHS yellow green group (near 144 A to 146 C).

*Color underside of sepals*.—RHS yellow green group (near 142 C to 144 D).

*Number of sepals per flower*.—The calyx presents 9 to 11 sepals with lanceolate shape and 3 to 4 sepals in addition smaller than above mentioned with less shape.

*Average fruit weight* (*April* 29).—24 g/Fruit.

*Average fruit weight* (*May* 17).—18 g/Fruit.

Disease resistance: No particular sensitivity to any disease or parasite has been observed for 'Dream'.

Cold tolerance: Given the capacity of plant to develop and to produce fruits below a temperature of 7° C. of temperature, the cold tolerance of 'Dream' is High.

Drought tolerance: Applicant has not made any test about drought tolerance.

What is claimed is:

1. A new and distinct strawberry plant of the variety substantially as shown and described.

* * * * *